ved by the United States
United States Patent [19]

Sapienza et al.

[11] Patent Number: 4,904,700

[45] Date of Patent: Feb. 27, 1990

[54] IRON CATALYST FOR PREPARATION OF POLYMETHYLENE FROM SYNTHESIS GAS

[75] Inventors: Richard S. Sapienza, Shoreham; William A. Slegeir, Hampton Bays, both of N.Y.

[73] Assignee: The United States of America as represented by the United States Department of Energy, Washington, D.C.

[21] Appl. No.: 327,465

[22] Filed: Mar. 22, 1989

Related U.S. Application Data

[62] Division of Ser. No. 175,781, Mar. 31, 1988, abandoned.

[51] Int. Cl.$^4$ .......................... C07O 1/02; C07O 1/10
[52] U.S. Cl. .................................... 518/700; 518/711; 518/721; 502/262; 502/326; 502/327
[58] Field of Search ........................ 518/700, 711, 721

[56] References Cited

U.S. PATENT DOCUMENTS 4,518,714  5/1985  Gustafson ........................... 518/721
4,622,308  11/1986  Koikeda et al. .

FOREIGN PATENT DOCUMENTS

86/01499  3/1986  World Int. Prop. O. .......... 502/326

Primary Examiner—Howard T. Mars
Attorney, Agent, or Firm—Hugh G. Glenn; Margaret C. Bogosian; William R. Moser

[57] ABSTRACT

This invention relates to a process for synthesizing hydrocarbons; more particularly, the invention relates to a process for synthesizing long-chain hydrocarbons known as polymethylene from carbon monoxide and hydrogen or from carbon monoxide and water or mixtures thereof in the presence of a catalyst comprising iron and platinum or palladium or mixtures thereof which may be supported on a solid material, preferably an inorganic refractory oxide. This process may be used to convert a cabon monoxide containing gas to a product which could substitute for high density polyethylene.

6 Claims, No Drawings

IRON CATALYST FOR PREPARATION OF POLYMETHYLENE FROM SYNTHESIS GAS

The U.S. Government has rights in this invention pursuant to contract number DE-AC02-76CH00016 between the U.S. Department of Energy and Associated Universities, Inc.

This is a division of application Ser. No. 175,781, filed Mar. 31, 1988, now abandoned.

FIELD OF THE INVENTION

This invention relates to a process for synthesizing hydrocarbons, more specifically long chain hydrocarbons known as polymethylene, by the reaction of carbon monoxide and hydrogen or carbon monoxide and water or mixtures thereof in the presence of a catalyst. Such polymethylene materials are suitable for use as diesel or jet fuels. More particularly, this invention relates to novel catalysts composed of iron and platinum or palladium or mixtures thereof which catalyze the reaction of CO and $H_2$ to yield polymethylene. Also covered in this invention are methods for the preparation of such catalysts and methods for use of such catalysts.

DESCRIPTION OF THE PRIOR ART

The synthesis of polymethylene (highly linear polyethylene) is conventionally made by the polymerization of ethylene. Pichler et al. reported in *Chem.*, 22: 257–285 (1948) that this route could be by-passed by passing carbon monoxide and hydrogen over a supported ruthenium catalyst. However, it was not until 1963 that a product of commercial interest was synthesized using this approach, a product that has properties very similar to high-density polyethylene [Pichler, *Brenstoff-Chemie*, 94, 33 (1963)]. The Pichler synthesis requires low temperature (100°–120° C.) and extremely high pressures (1000–2000 atm) to achieve a high degree of polymerization. Of the various catalysts tested in the Pichler process, only ruthenium catalyzed the carbon monoxide and hydrogen reaction to bring about significant conversion to macromolecules. Other catalysts tested produced oils and paraffin waxes. Evaluations of the economics of this high-pressure, ruthenium catalyzed synthesis have shown that unless catalyst activity is increased, the process is not of practical interest because the cost of the ruthenium and the required pressures have a negative impact on the economics of the process.

Iron-based catalysts for hydrocarbon synthesis are also known but ordinarily afford only modest activity and tend to favor the production of medium molecular weight olefinic products. These catalysts have been well studied and a discussion of their utilization is set forth in "Fisher-Tropsch and Related Synthesis", H. Storch et al., published by John Wiley & Son, New York.

The so-called Fischer-Tropsch synthesis, wherein liquid aliphatic hydrocarbons, alcohols and minor amounts of aldehydes, fatty acids and ketones are produced by the catalyzed hydrogenation of carbon monoxide, has been used for over fifty years. Numerous attempts have been made to refine this synthesis in terms of improved effectiveness of the catalyst, product yield, improved production of more desirable product fractions, and control of the product distribution. Additionally, efforts have been made to achieve more stable catalysts.

As a general rule, the materials which have been known to be effective as Fischer-Tropsch catalysts are extremely sensitive to air and moisture and consequently, must be used either shortly after preparation or prepared in situ. In more recent years, the catalysts used for such reactions were composed of cobalt, sometimes in conjunction with nickel on a support, such as a clay. These catalysts have generally been characterized by instability and low activity. Additionally, such catalysts required the use of either a fixed or fluidized bed type system. Such contacting methods often produce severe heat transfer problems which place an additional burden upon the process as well as affect the uniformity of the products obtained.

The present invention system appears much more active with a molecular weight distribution oriented toward polymer useful aliphatic hydrocarbons. Unlike ruthenium catalysts, the invention system is relatively inexpensive and is effective at modest pressure, yet displays activity comparable to ruthenium. The catalyst displays low consumption ratios and low methane yields.

SUMMARY OF THE INVENTION

We have discovered a novel catalytic system which can be used for the synthesis of hydrocarbons, particularly long chain hydrocarbons known as polymethylene, from carbon monoxide and hydrogen or from carbon monoxide and water or from mixtures thereof. This catalytic material is unique in both its physiochemical constitution as well as the properties which it exhibits. The catalytic composition of the present invention exhibits activity comparable to the prior art ruthenium catalyst. However, unlike the ruthenium catalyst, the present catalyst is relatively inexpensive and is effective at moderate pressure. In addition, such activity can be obtained in slurry form which substantially improves the heat transfer factors involved in the Fischer-Tropsch synthesis. Furthermore, the catalytic composition of the present invention exhibits superior stability and can be stored for long periods of time in either a dry or slurry form. Finally, the catalytic composition of the present invention produces a very desirable product composed of a major fraction of long-chain hydrocarbons resembling commercial polyethylene.

The catalyst compositions of the present invention comprise iron with platinum or palladium or a mixture of platinum and palladium in a dispersed state, with the iron being deposited on the palladium and/or platinum. The platinum or palladium or mixtures thereof may be supported on a solid phase. Iron comprises at least 40 weight percent and platinum or palladium at least 1 weight percent, based on total catalyst weight. Preferably, the catalyst composition of the present invention comprises from 40–60% iron and from 1–2% platinum and/or palladium.

The catalyst of the present invention is easily prepared by a new process which also comprises a part of the present invention. This process allows the composition to be prepared and either used in situ or separated for use at a later time.

The method and use of the present invention is also unique as compared with conventional Fischer-Tropsch catalysts. Of great importance is the fact that this catalyst can be used in dilute slurry form and with dilute concentrations of reactants to obtain high yields of desirable product fractions. This avoids the heat transfer problems commonly encountered with alternative contact systems.

The reaction of carbon monoxide and hydrogen and/or water catalyzed by the catalyst system of the instant invention at temperatures of about 225° C. yields a mixture of hydrocarbons, the major portion of which is a polymethylene material which is xylene or cyclohexane insoluble, melts at about 108°–112° C. and softens at 108° C. This product is comparable to commercial high density polyethylene, which usually shows a melting point of 109°–110° C. and softens at 88° C. Additionally, the instant catalyst system is able to operate effectively under mild pressure and temperature conditions and can also operate effectively under dilute feed gas conditions, that is in the presence of synthesis gas diluents or impurities, such as nitrogen.

DETAILED DESCRIPTION OF THE INVENTION

The present invention relates to a process for the synthesis of polymethylene from carbon monoxide and hydrogen and/or water, preferably in the form of steam, at modest pressure. In this process, the feed stream is contacted with a catalyst comprising iron deposited on platinum and/or palladium, where the platinum and/or palladium may or may not be supported on a suitable solid phase, preferably an inorganic oxide like alumina. In this process many carbon-carbon bonds are formed with concurrent formation of carbon-hydrogen bonds. The oxygen of the carbon monoxide is rejected mainly as water when hydrogen is a sufficient co-reactant and as carbon dioxide when steam is a co-reactant.

The unique catalytic composition of the present invention is obtained by a novel stepwise process. Preferably, the palladium and/or platinum metal(s) is deposited on a solid phase using conventional deposition techniques.

Typically, this is accomplished by impregnation of the support with an aqueous solution of a salt of the particular metal; suitable salts for this purpose include salts of chloroplatinic acid, palladium chloride, ammonium chloroplaninate, and the platinum amine salts. For example, such preparations are shown in U.S. Pat. No. 3,988,334, incorporated herein by reference.

The support or carrier or solid phase material may be chosen from any appropriate material such as talc, dolomite, limestone, clay, activated carbon, pumice, the oxides or hydroxides of zinc, chromium, magnesium, calcium, titanium, or zirconium, barium sulfate, alumina, silica, zirconia, silica-aluminas such as zeolites, kieselguhr, and the like. The preferred supports are alumina, silica, zeolite, kieselguhr, zinc oxide, and thorium oxide. The support material is typically used in the form of spheres, granules, powders, pellets or extrudates. The support is immersed in an aqueous solution of a salt of the particular metal. After sufficient time for impregnation of the support, the mixture is dried at temperatures between 80°–200° C., usually in air, and ultimately calcined in air for a period from one half to one and one half hours at temperatures between 300°–600° C. Those skilled in the art will readily recognize that other methods are available, such as the known techniques of sputtering, precipitation, vapor deposition, electrical deposition and electrochemical deposition.

Iron impregnation or precipitation should follow formation of the platinum and/or palladium component. This sequential technique is generally favored over a co-impregnation using a single solution comprising precursors for all metals because it insures that the iron component will be deposited on the platinum and/or palladium component.

The essential ingredient of the present catalytic composite is the iron component. The supported platinum and/or palladium metal promoters alone are not effective in converting carbon monoxide and hydrogen to long chain hydrocarbons. The iron component may be deposited onto the supported platinum and/or palladium component in any suitable manner known to those skilled in the catalyst formulation art to result in a relatively uniform distribution of the catalytically available iron. Suitable deposition techniques include precipitation, gelation and impregnation.

One such deposition approach involves the addition of an iron precursor compound, a soluble, decomposable and reducible compound of iron, such as iron nitrate, iron acetate, or iron oxalate, to the platinum and/or palladium metal component, which may be supported or unsupported.

The solvent used for the iron deposition step may be water, alcohol, ether or any other suitable organic or inorganic solvent provided the solvent does not adversely interact with any of the other ingredients of the composite or interfere with the distribution and reduction of the iron component. The preferred solvent is water.

Alternatively, the supported platinum and/or palladium component can be used as a carrier for a precipitated iron oxide. When combined with the other components of the catalyst, the iron metal component may be in elemental or alloy form and may be used as such. The iron and platinum or palladium components exist as separate but interacting crystallites of the individual metals.

The iron impregnated component, when sufficiently dried, is calcined at a temperature of about 400° C. and then contacted in a reducing atmosphere, as by contact with a stream of hydrogen, to reduce the iron precursor to the desired metallic form.

Optimum catalyst performance is obtained when the catalyst is prepared in the manner described above. At least 40 weight percent iron and 1 weight percent platinum and/or palladium must be present in the catalyst material for optimum performance. Total metal concentration of the catalyst should be from 40–100%.

After the catalyst is contacted with the reducing atmosphere, the catalyst, still in particulate form, can be separated from the solvent by standard separation techniques, e.g., magnetic techniques, precipitation, filtration, centrifugation, and the like. The catalyst can then be stored either in the moist form or after having been dried at relatively low temperatures, i.e., under 300° C., and preferably under 120° C., for extended periods of time without any additional precautions being taken. Thus, the catalyst of the present invention does not lose its activity as a result of contact with air, even after long periods of time on the shelf.

The catalyst of the present invention can be used to synthesize long-chain hydrocarbons from hydrogen and carbon monoxide or water and carbon monoxide or mixtures thereof by contacting the gaseous mixture with an effective amount of catalyst.

The method of use of the present catalyst is also novel and advantageous. Not only can the present catalyst be used in the conventional so-called fixed bed or fluidized bed reactors, but it can also be used in a slurry type reactor. The conventional contacting techniques, i.e., fixed or fluidized bed, suffer from the disadvantages that localized hot spots can develop due to poor heat transfer and the relatively high concentration of catalyst. This can affect both the efficiency of the process and the product distribution and uniformity. When the catalyst of the present invention is used in the slurry type reactor, the catalyst can be used in relative dilute form and can also be used efficiently with dilute gaseous mixtures.

In one preferred embodiment, the catalyst of the present invention can be utilized in slurry form in the conventional solvents used for such reactions. Suitable solvents include, for example, saturated hydrocarbons of 8–16 carbon atoms, such as n-octane and n-decane, aliphatic alcohols, such as butanol and osooctanol, aldehydes, the alcohol or ether by-products of the oxyl process, such as isobutanol, and ethers, or mixtures of any such solvents. Preferred solvents are hexadecane and xylene. The slurry concentration can generally be in the range from about 1.0 to 50 percent by weight. This can, of course, be varied depending on the desired results. Slurry concentrations of from about 1 to 300 g/l are preferred and particularly preferred is a slurry concentration of about 20% by weight.

Suitable temperatures for using the present catalyst in a synthesis reaction range from about 100° to 300° C., and, preferably, are in the range from about 130° to 250° C. The catalyst in the solvent is subjected to pressure using carbon monoxide and hydrogen. The process can be carried out under either a static pressure or in a continuous manner. Typically, the pressure utilized is between about 500 to 5000 psi and the mixture is agitated at a temperature from about 130° to 250° C.

In the static situation, the entire mixture is placed into a pressure bomb which is agitated as by shaking. Alternately, an internal mixing or stirring device can be utilized. In so far as the gaseous composition utilized in the process is concerned, one can use a ratio of hydrogen to carbon monoxide in the range from about 1:10 to 10:1, and preferably in the range from 2:1 to 1:2.

While it is possible to prepare the present catalyst in the manner noted above and isolate the catalyst for storage and subsequent use, it is also possible to utilize the catalyst after it has been prepared in situ. In such a case, the catalyst would be prepared in the manner described hereinabove and one would simply continue to maintain the temperature and pressure conditions along with the appropriate amount of agitation to produce reaction of the gaseous materials and synthesis thereof into the desired hydrocarbons. The reaction is normally followed by continuous measurement of the pressure. When the pressure ceases to decrease, i.e., remains constant or decreases only slowly, it is apparent that the reaction is ceasing and the desired polymethylene has been produced. This product can be isolated in the normal manner.

The catalysts of the present invention, their method of preparation and use are shown in the following examples:

EXAMPLE 1

Ten grams of 5% palladium on alumina was dispersed in 300 ml of distilled water by means of a magnetic stirrer. Eighty-one grams of iron nitrate was added and the mixture heated to boiling. A solution of 16 g potassium hydroxide in 300 ml of a 1.0M potassium carbonate solution was likewise heated to boiling. The latter solution was added to the former and stirring continued for 30 min. The black-brown colloidal precipitate was carefully filtered and washed sequentially with 2 liters of boiling water. The filter cake was dried overnight and carefully powdered to afford 27 g red-brown unreduced catalyst.

The catalyst (1.25 g) was reduced at 200° C. for 3 hours in a stream of hydrogen. A 300 ml stirred autoclave containing 200 ml xylene was purged with argon; the black, reduced catalyst was added after cooling. The autoclave was charged with 1600 psi synthesis gas containing 55% $H_2$ and heated at 150° C. Thirty-five minutes were required to reach desired temperature. The reactor was maintained at this temperature for the next 40 minutes, during which time little pressure change was observed.

The temperature was then increased to 180° C. over the next 10 min. During the following 30 minutes, little pressure change was observed. The reactor was then heated to 225° C. Over the next 2.5 hours the pressure decreased 450 psi. Filtering off the catalyst and evaporating the xylene left an off-white waxy material. Analysis of the material showed it was xylene insoluble, had a m.p. of 108°–112° C., and softened at 108° C., comparable to commercial samples of polyethylene.

The activity of the catalyst was 16 psi/min (from 1880–995 psi over 55 minutes) at 225° C.; it was 13 psi/min on average if the reaction is conducted at room temperature. The catalyst activity in terms of hydrocarbon production is approximately 25 $\mu$mol hydrocarbon produced/g metal/second. The consumption ratio was 1.4 (86% CO consumed in 55 min.). The yield of the polymethylene material was about 40% (of 100 mmol-($CH_2$)-obtainable from syngas consumed). The gaseous products produced along with the polymethylene were $CO_2$, $CH_4$, $C_2H_4$ and $C_2H_6$.

EXAMPLE 2

Five grams of alumina was suspended in 5 g water. A solution of 0.44 g $PdCl_2$, 7 ml hydrochloric acid and 10 ml water was added. The slurry was heated with stirring to dryness on a hot plate, then dried at 120° C. for 16 hrs. The resulting solid was carefully ground and then reduced for 2 hrs. at 220°–250° C. under a stream of $H_2$.

Two grams of this material and 16.2 g $Fe(NO_3)_3.9$-$H_2O$ were added to 50 ml of boiling water. While stirring, 100 mmol of $Na_2(CO)_3$ dissolved in 100 ml of water was added. Boiling continued for another 15 min., at which time the slurry was filtered hot. The precipitate was repeatedly washed with hot water, until the washings were free of dissolved salts. The precipitate was then pressed dry and stored overnight in an oven at 120°.

A sample of 2.5 g of the red-brown powder was reduced with $H_2$ in a tube furnace at 220° for 2 hrs. The activated catalyst was added to a 0.3 liter pressure reactor containing 100 ml cyclohexane. The reactor was purged with syngas, then charged with 750 psi $H_2$ and 375 psi CO.

Heating was commenced and the pressure had increased to 1890 psi when 225° was achieved. During the next hour, this temperature was maintained and the pressure was found to decrease uniformly, affording an average contraction of 16 psi/min. The remaining gas, after cooling, was found to contain 169 mmol $H_2$, 31 mmol CO, 43 mmol $CO_2$, 9 mmol $CH_4$, 0.8 mmol $C_2H_4$ and 0.6 mmol $C_2H_6$ indicating 86% consumption of carbon monoxide and a consumption ratio of 1.4 ($H_2$/CO). The liquid phase from the reactor containing a waxy insoluble.

The catalyst was separated from the liquid phase with the help of a magnet. When washed with toluene and dried, 2.3 g of catalyst was recovered.

Analysis of the liquid phase by gas chromatography indicated only small amounts of volatile (b.p. <250°) products. The slightly off-white waxy insoluble material (about 0.5 g) was collected on a fritted funnel. This was partially soluble in hot xylene. An infrared spectrum (KBr) of this material was identical to that of polyethylene. The material was found to melt in the range 108°–112° C., suggesting properties similar to those of commercial polyethylene.

We claim:

1. A method for synthesizing polymethylene comprising contacting a mixture of hydrogen and carbon monoxide or water and carbon monoxide or mixtures thereof in a solvent with a slurry of a catalyst composed of palladium or platinum or mixtures thereof supported on a solid phase with iron deposited thereon wherein iron comprises at least 40 weight percent and platinum or palladium or mixtures thereof comprise at least 1 weight percent based on the total catalyst weight, under conditions sufficient to convert the gaseous mixture to polymethylene.

2. The method of claim 1, wherein the support is selected from the group consisting of alumina, silica gel, kieselguhr and zinc oxide.

3. The method of claim 1, wherein the slurry concentration is in the range from about 1.0 to 50 percent by volume.

4. The method of claim 1, wherein the reaction is carried out at a temperature from about 100° to 300° C.

5. The method of claim 4, wherein the temperature is from about 130° to 250° C.

6. The method of claim 1 wherein the solvent is selected from the group consisting of cyclohexane and xylene.

* * * * *